United States Patent
Draughn

[19]

[11] Patent Number: 6,155,439
[45] Date of Patent: Dec. 5, 2000

[54] LAPAROSCOPIC-RACK INSTRUMENTS HOLDER

[75] Inventor: David G. Draughn, Gastonia, N.C.

[73] Assignee: Flexbar Machine Corp., Islandia, N.Y.

[21] Appl. No.: 09/255,307

[22] Filed: Feb. 22, 1999

[51] Int. Cl.$^7$ ................................................. A47F 7/00
[52] U.S. Cl. ................................................. 211/85.13
[58] Field of Search .......................... 211/85.13, 70.6;
206/349, 363; 422/300

[56] References Cited

U.S. PATENT DOCUMENTS

| | | | |
|---|---|---|---|
| 3,774,773 | 11/1973 | Brent | 211/70.6 |
| 3,776,387 | 12/1973 | Brent | 211/70.6 |
| 4,641,749 | 2/1987 | Link et al. | 211/70.6 |
| 4,690,285 | 9/1987 | Stone | 211/70.6 |
| 5,046,624 | 9/1991 | Murphy et al. | 211/70.6 |
| 5,201,430 | 4/1993 | Artzer | 211/70.6 |
| 5,449,069 | 9/1995 | Pijanowski et al. | 211/70.6 |
| 5,533,618 | 7/1996 | Pickels, Jr. | 206/363 |
| 5,913,430 | 6/1999 | Gobel et al. | 211/70.6 |

*Primary Examiner*—Alvin Chin-Shue
*Assistant Examiner*—Sarah Purol
*Attorney, Agent, or Firm*—Charles I. Brodsky

[57] ABSTRACT

An instrument holder which provides rapid and secure positioning of any diameters of laparoscopic instruments through the use of a specially designed grid in a cantilevered-style rack by employing, in a preferred embodiment, a pair of double swivel-ball locking positioners with an adjustable clamp for securement to an operating room table rail, with the grid having front and rear sides having upwardly and downwardly extending holding bars, respectively, of spaced notch segments between which the cannulas of the instruments extend, in adjusting the angle and attitude of the grid and instruments, and the height of the instruments about and above the surgical field.

16 Claims, 4 Drawing Sheets

6,155,439

LAPAROSCOPIC-RACK INSTRUMENTS HOLDER

FIELD OF THE INVENTION

This invention relates to laparoscopic instruments as employed in an operating room environment, in general, and to a universal holder for presenting the laparoscopic instruments for easy and convenient access, in particular.

BACKGROUND OF THE INVENTION

The disadvantages inherent in conventionally placing surgical instruments on a tray adjacent to an operating field have been described in U.S. Pat. No. 5,451,380 to Zinnanti. The particular disadvantages associated with delivering large laparoscopic instruments to the operating area is there discussed as well. The solution proposed in this Zinnanti patent is to provide a tray system structure with sides and notch cross bars to position the laparoscopic instruments with their handles hanging down next to one another, so that a plurality could be arranged in adjacent placement, and in which the different types of laparoscopic instruments are held in position during assembly, sterilization, transportation and storage. While such a tray system may act adequately well, experience has shown that it does not go far enough in allowing for rapid and secure positioning of the laparoscopic instruments above the surgical field. As will be appreciated, such a feature would provide the surgeon quick and easy access to these instruments without the need for having to reach across the table or having to look away from the observing monitor to grasp onto the instrument needed. Further advantages will be seen by arranging the instruments so that their positioning can be continually adjustable in all 3 dimensions to include angle, height, and rotation—and, with the system being easily portable and autoclavable. Additional advantages will follow in an environment that significantly reduces, or in some cases eliminates, the dependence on a scrub technician, or frees the assistant to concentrate on other delegated tasks, besides creating additional room around the operating field. Not only will increased operating efficiency result, but the requirements for ancillary personnel could be reduced at the same time—all the while allowing for the positioning of the surgical instruments exactly where they are most needed. Thus, something beyond a mere laparoscopic instrument tray of U.S. Pat. No. 5,451,380 would be desirable to have.

SUMMARY OF THE INVENTION

As will become clear from the following description, the laparoscopic-rack universal instrument holder of the invention provides rapid and secure positioning of any diameters of laparoscopic instruments through the use of a specially designed grid in a cantilevered-style rack. In particular, a pair of double swivel-ball locking positioners are employed along with an adjustable clamp for securement to an operating room table rail. Each positioner, to accommodate this, can be swung to any desired point 360°, before being locked in place.

In accordance with a preferred embodiment of the invention, the laparoscopic-rack can be of a dimension to hold up to eight instruments at a time ("full rack"), or up to four instruments ("half rack"). In this preferred embodiment, the rack has front and rear sides which incorporate holding bars in slotted channels to hold the cannula in position,—although other alternative configurations could simply allow the cannulas to be temporarily supported. Thus, and as will be seen, the front side of the rack includes a holding bar which extends upwardly, while the rear side includes a downwardly extending holding bar. In the "full rack" embodiment of the invention, a cross bar extends between the front and rear sides, in receiving a post coupled with one of the two double swivel-ball locking positioners, while in the "half rack" frame, such cross bar constitutes one of the two sides of the rack.

BRIEF DESCRIPTION OF THE DRAWINGS

These and other features of the present invention will be more clearly understood from a consideration of the following description, taken in connection with the accompanying drawings, in which.

DETAILED DESCRIPTION OF THE INVENTION

Figure 1:
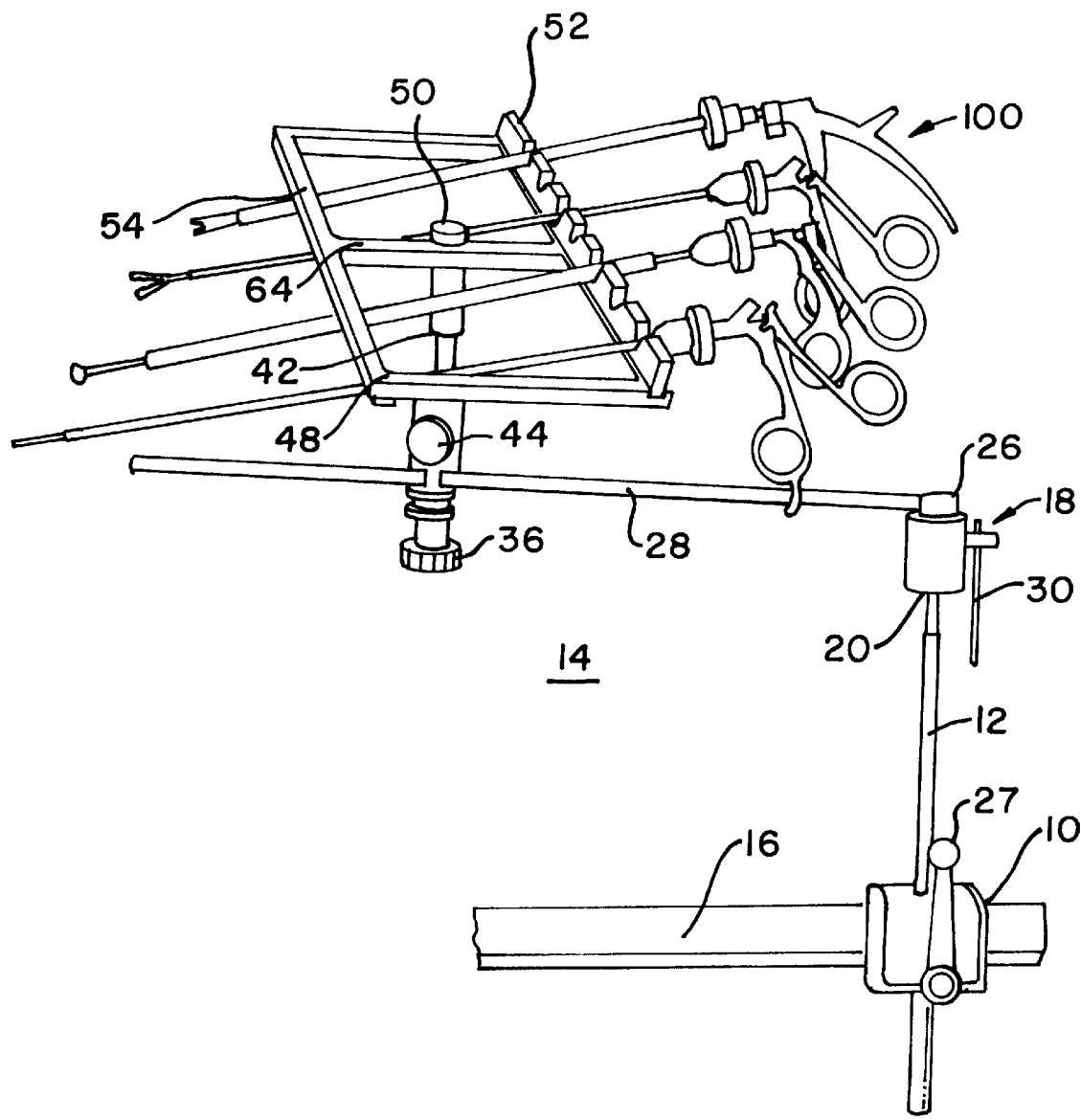
FIG. 1 is a perspective view of the laparoscopic-rack universal instrument holder as it may be secured to an operating room table in use.

As will be readily appreciated by those skilled in the art, the laparoscopic-rack universal instrument holder of the invention allows for the providing of quick and easy access to instruments exactly where the surgeon requires them. As will be understood, its use facilitates the arrangement for such procedures as laparoscopic cholecystectomy, laparoscopic appendectomy, laparoscopic hernia repair, laparoscopic Nissen Fundoplication and other advanced procedures including gynecologic, urologic and thorasoscopic procedures. As will also be acknowledged, the lap-rack frame essentially comprises a grid to hold such items as "all-size" laparoscopic instruments, suction irrigation devices, staple & clip appliers, 5 mm or 10 mm scopes with cameras—and just about any required instrument to be rapidly and securely positioned above a surgical field. Scissors, graspers, forceps, dissectors, clamps, needle holders, clip appliers, fan retractors, cautery devices and stapling devices can be easily and conveniently thus positioned and held.

Thus, referring to the drawings, a clamp 10 first receives a post 12, for clamping the instrument holder of the invention 14 to the operating room table rail, indicated by the reference numeral 16. A first double swivel-ball locking positioner 18 receives the post 12 at its lower end 20. A right-angle notch 22 (for 90° positioning), is located at the lower end 20 and upper end 26 of the double swivel-ball locking positioner 18, for receiving a second post 28 which can be swung to any point 360°. Once the post 12 is clamped to the operating room table rail 16 at an adjustably desired height, it is fixed in position, as by a locking handle 27. Once the posts 12 and 28 are adjusted to the desired angle and attitude, they, too, are similarly fixed in position, and by the locking handle 30—which cooperate with precision angled bearings to interface with the posts in known manner. Such a double swivel-ball locking positioner is readily available—as, for example, from Flexbar Machine Corp., of 250 Gibbs Road, Islandia, N.Y. The rail clamp assembly is illustrated as 75 in FIG. 2, with the mounting post assembly shown as 77.

As previously mentioned, the laparoscopic-rack holder of the invention can be sized to hold up to eight instruments ("full rack"), or up to four instruments ("half rack"). Such "full rack" instrument frame is shown at 79 in FIG. 2, while the "half rack" instrument frame is shown at 81. Both "racks" 79 and 81 cooperate with an attachment clamp 32 for receiving the post 28, and which includes its own double swivel-ball locking positioner 34. A control knob 36 of any appropriate design is releasably securable in understood manner to lock the post 28, with the double swivel-ball positioner 34 being provided with yet another right angle notch 38 at its upper end 40, to allow for an additional 360° swing to its own post 42 when receiving the lap-rack frame 79 or 81. As with the double swivel-ball positioner 18, the fixing of the post 42 once positioned is attained through a lock mechanism, indicated as the adjustable knob 44.

Figure 2:
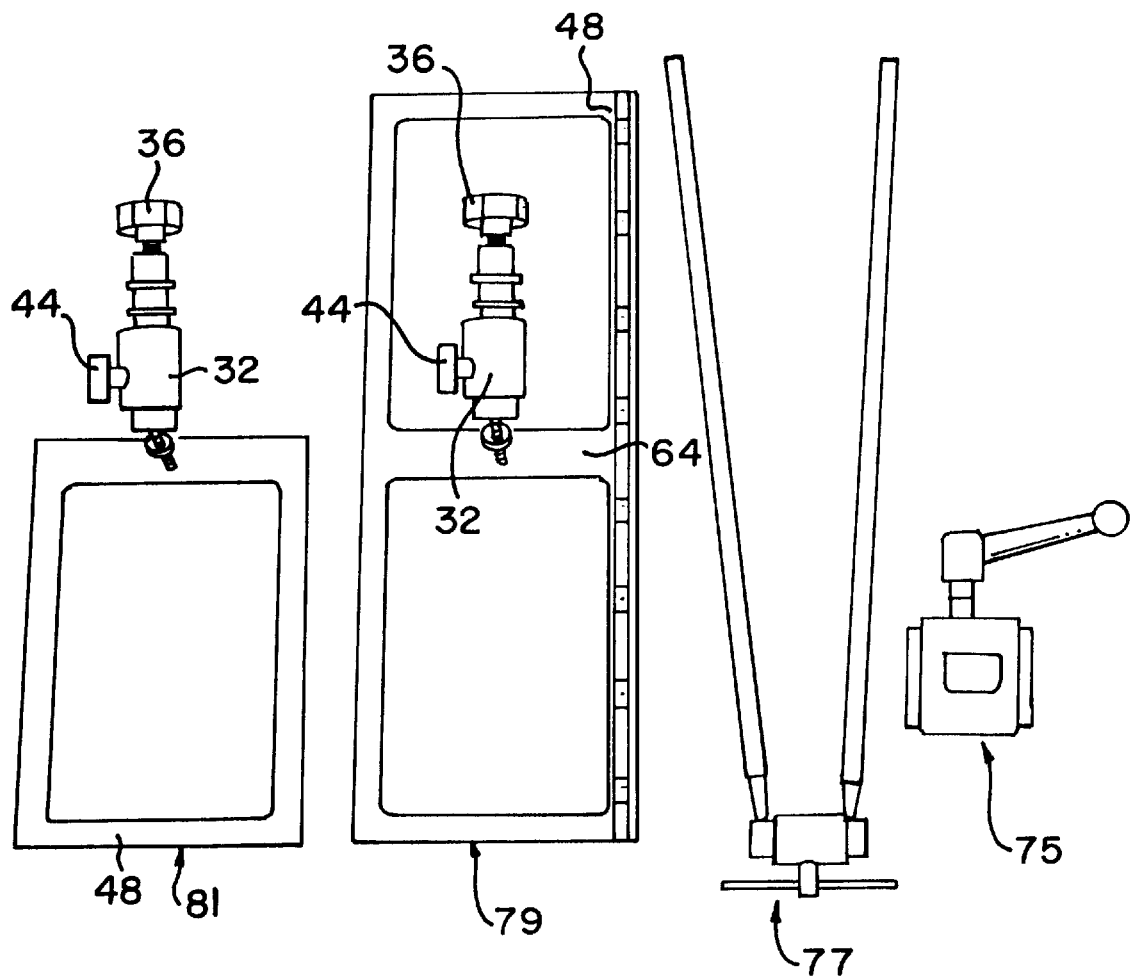
FIG. 2 is a perspective view of the component parts of the instrument holder embodying the invention as they might be shipped, ready for installation.
Figure 3:
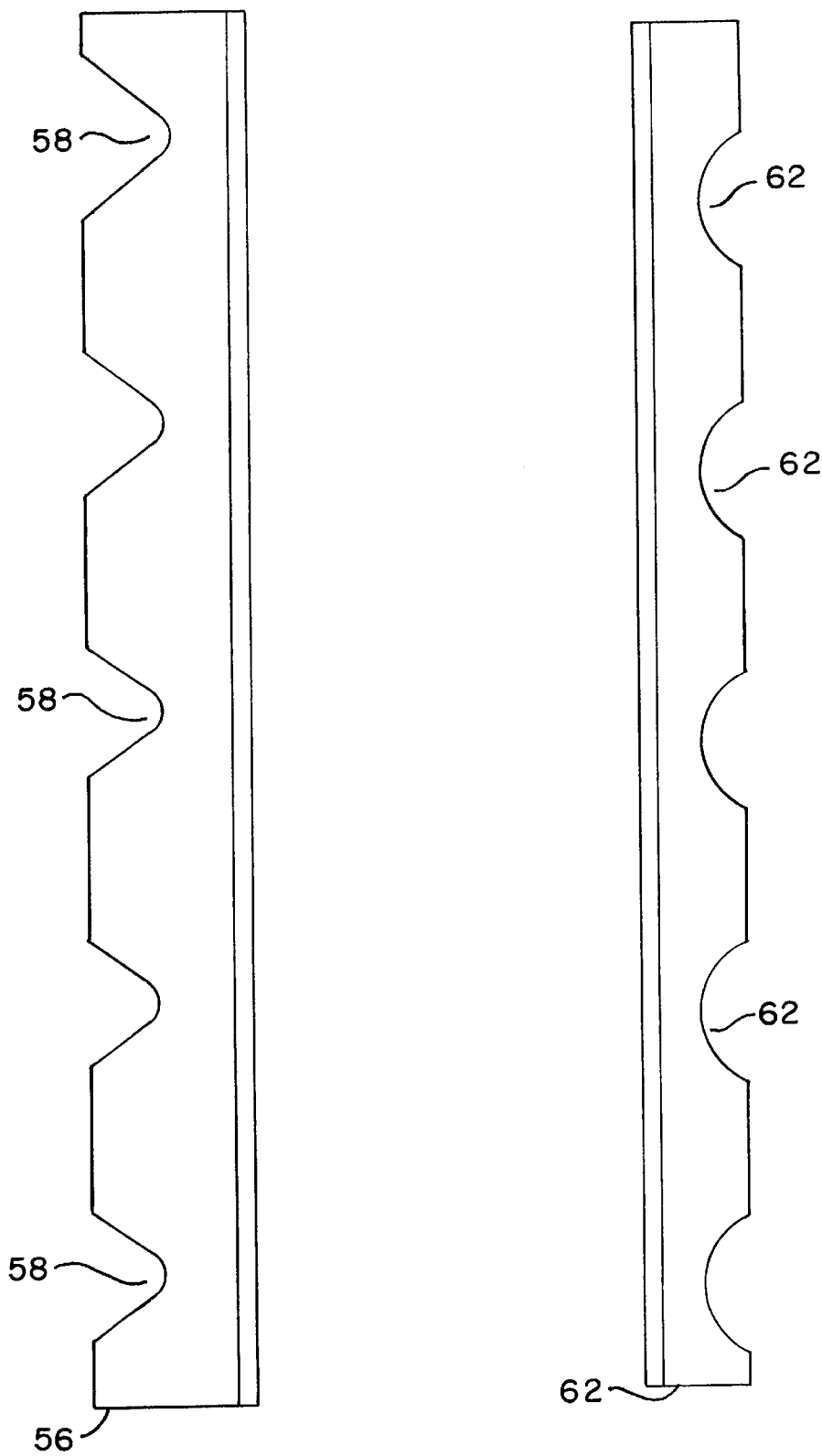
FIG. 3 are front views of a pair of instrument holding bars which are fitted into the lap-rack frame of FIGS. 1 and 2, for securely holding the various laparoscopic instruments in position.
Figure 4:
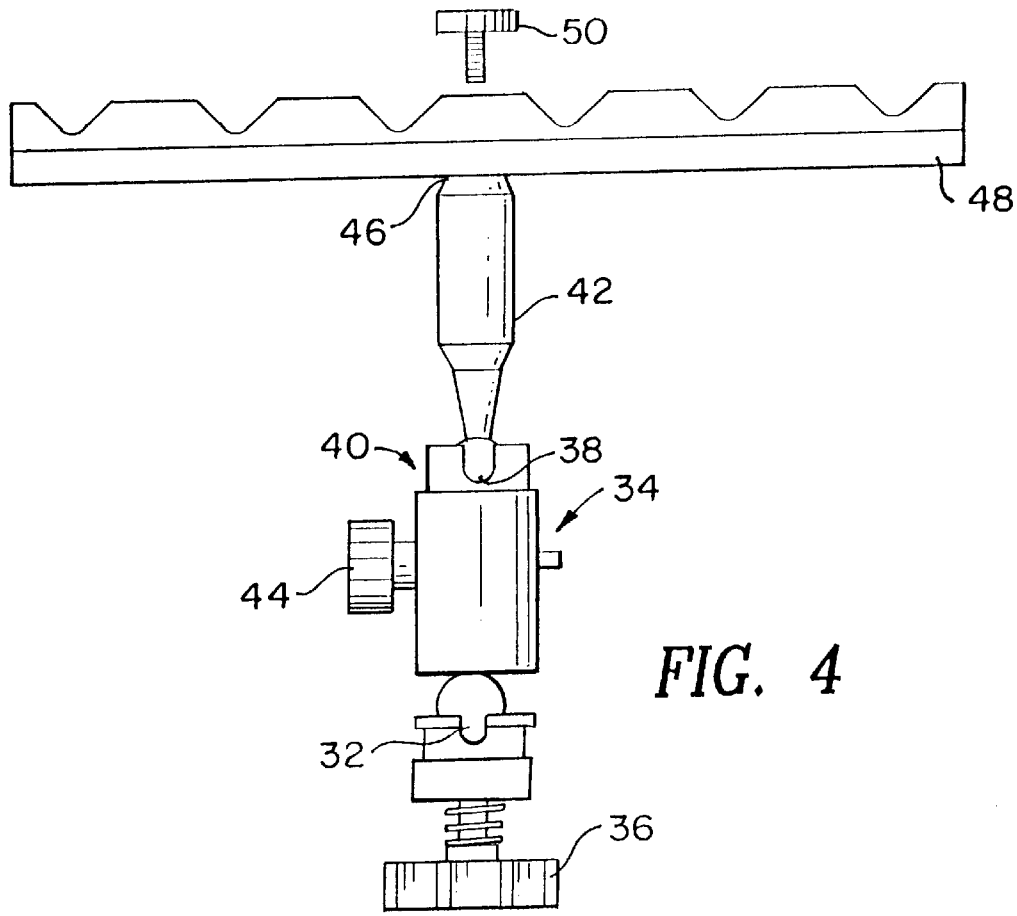
FIG. 4 is an illustration helpful in an understanding as to how a first double swivel-ball locking positioner of the invention cooperates with the lap-rack instrument frame to allow for easy access to all instruments without the surgeon's having to reach across the operating room table or to look away from a video monitor in order to grasp the instrument.
Figure 5:
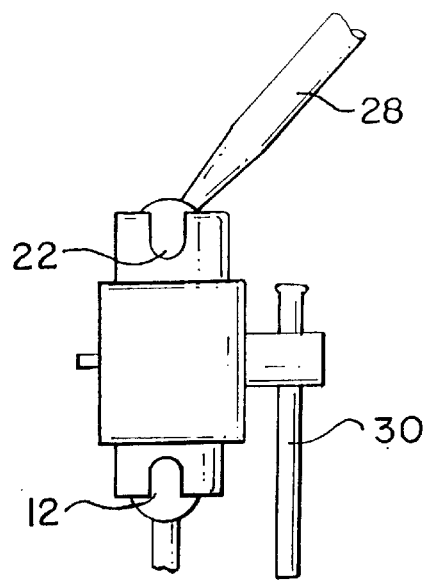
FIG. 5 is an illustration helpful in an understanding of how a second double swivel-ball locking positioner secures the instrument holder to the operating room table rail, so as to allow the lap-rack instrument frame and system to be positioned at an infinite number of attitudes and angles—and which also allows the mounting post to fold up for storage, sterilization and dismantling.

The post 42, in turn, concludes with an inwardly threaded aperture which fits within a recess at an underside 46 of the frame grid 48 to receive an externally threaded knob 50 in securing the frame grid 48 in position. The front side 52 of the frame grid 48 is slotted open from the top, while the rear side 54 of the frame grid 48 in a preferred embodiment of the invention is slotted from the bottom. A first segmented instrument holding bar 56 seats within the upward extending slot of the frame front 52, as shown in FIG. 3, with a generally V-shaped notch 58. A second segmented instrument holding bar 60 seats within the downward extending slot of the frame rear 54, as similarly shown, with a generally U-shaped notch 62. As illustrated in FIGS. 1 and 2, a cross bar 64 extends between the front and rear sides 52, 54 to receive the post 42 for the "full rack" frame. For the "half rack" frame of FIG. 2, the post 42 runs through an aperture along the frame, between the front and rear sides 52, 54.

In the complete "full rack" system of FIG. 1, the various laparoscopic instruments 100 are in place, ready for use. As will be understood, optimum orientation and use follows from adjusting the operating room table clamp 10 to set the post 12 to desired height, from orienting the double swivel-ball locking positioners 18 and 34 to the angle and attitude desired and locking the handle 30 and control knob 44 in position, and from orienting the post 42 for placement of the rack frame 48, before tightening it with the adjustable knob 44. Then, inserting the various laparoscopic instruments, the suction/irrigators, the staple devices and clip appliers, the appropriate scopes with their camera attachments, etc.—or other devices as the instruments 100—a cantilevered-style grid arrangement results in providing the surgeon the required quick and convenient access to the instruments without having to reach across the table to locate them, or having to look away from the monitor in use when trying to grasp the instruments, as they are already there.

In the preferred embodiment of the invention, furthermore, and in its usage, the heavier end of the laparoscopic instrument will be understood to rest on top of a concave V notch 58 of the instrument holding bar 56 at one parallel arm (i.e., the "front" 52 of the frame grid 48), and to extend beneath a convex U notch at an opposing parallel arm (i.e., the "rear" 54 of the frame grid 48). As a result, the weight of the heavier portion of the instrument (i.e., the portion normally held by the surgeon) presses downwardly over the concave V notch portion 58 of the front 52 of the frame 48, pivoting the far end of the instrument upwardly against the convex U notch portion 62 of the opposing rear 54. Such pivoting forces serve to hold the instrument in place in the frame grid 48, while minimizing contact between the instrument and the frame itself. The holding bars 56 and 60 may each be fabricated of silicon.

While there has been described what is considered to be a preferred embodiment of the present invention, it will be readily appreciated by those skilled in the art that modifications can be made without departing from the scope of the teachings herein of providing a system which allows the surgeon to easily position in attitude and angle that lap-rack frame which holds the instruments required for any surgical procedure. Thus, whereas a particular arrangement has been set forth for the operating room table clamp 10, as an example, other types of clamps may be employed as well. Similarly, while optimum control of angle and attitude in all planes is attainable through the employment of the second double swivel-ball positioner 34, in some instances a lesser degree of control might be accepted for maintaining the lap-rack frame 48 only in a single, for example, horizontal plane—as, by employing just a simple clamp for the post 28, in securing the frame 48, and foregoing the orientation capability afforded by the double swivel-ball positioner 34. While not as universal, it will be understood that even such arrangement allows for the controlled placement of the instruments within the surgical field, beyond the capability of systems presently used where additional operating room personnel hand the instruments to the surgeon and then retrieve them, or where the surgeon has to take his, or her, eyes from the viewing monitor, when reaching for the instruments. Such lesser control, although surrendering some of the infinite variations possible with the preferred embodiment, however, will continue to be seen within the principles set forth herein. And, whereas the invention has been described with respect to holding bars 56 and 60 having V-shaped notches 58 and U-shaped notches 62, respectively, it will be understood that the invention will continue to offer its advantages whether these notches be of this different cross-section or of the same cross section, as an alternative. For at least all the reasons, therefore, resort should be had to the claims appended hereto for a true understanding of the scope of the invention.

I claim:

1. Laparoscopic instrument holding apparatus for supporting laparoscopic instruments having a cannula about a surgical field, comprising:

first and second posts, each having opposing ends;

first means for securing one end of said first post to an operating room table rail;

a double swivel-ball positioner having a first right-angle notch for receiving the other end of said first post, and a second right-angle notch for receiving one end of said second post;

a frame grid having front and rear sides;

first and second holding bars respectively extending upwardly and downwardly from said front and rear sides of said frame grid;

a plurality of spaced notch segments in said first and second holding bars substantially opposite one another for receiving the cannulas of laparoscopic instruments extended therebetween to hold said instruments in place by cantilever action between said first and second holding bars of said frame grid; and second means securing the other end of said second post to said frame grid.

2. The apparatus of claim 1, wherein said spaced notch segments in said first and second holding bars are of substantially the same cross-section.

3. The apparatus of claim 1, wherein said spaced notch segments in said first and second holding bars are of substantially different cross-sections.

4. The apparatus of claim 1, wherein said spaced notch segments in said first holding bar are substantially V-shaped and wherein said spaced notch segments in said second holding bar are substantially U-shaped.

5. The apparatus of claim 1, wherein said front and rear sides of said frame grid are slotted to receive said first and second holding bars selectably insertable therein.

6. The apparatus of claim 1, wherein said second means secures said other end of said second post to said frame grid at a point along said grid between said front and rear sides.

7. The apparatus of claim 1, wherein said frame grid includes a cross-bar which extends between said front and rear sides of said grid, and wherein said second means secures said other end of said second post to said cross-bar.

8. The apparatus of claim 1, wherein said first means is adjustable for raising and lowering the height of said double swivel-ball positioner with respect to said operating room table rail.

9. The apparatus of claim 1, wherein said second means includes a second double swivel-ball positioner having a first right-angle notch for receiving said other end of said second post, and a second right-angle notch for receiving one end of an additionally included third post, an opposite end of which is rotatably coupled to said frame grid.

10. The apparatus of claim 9, wherein said spaced notch segments in said first and second holding bars are of substantially the same cross-section.

11. The apparatus of claim 9, wherein said spaced notch segments in said first and second holding bars are of substantially different cross-sections.

12. The apparatus of claim 9, wherein said spaced notch segments in said first holding bar are substantially V-shaped, and wherein said spaced notch segments in said second holding bar are substantially U-shaped.

13. The apparatus of claim 9, wherein said front and rear sides of said frame grid are selected to receive said first and second holding bars selectably insertable therein.

14. The apparatus of claim 9, wherein said third post couples to said frame grid between said front and rear sides thereof.

15. The apparatus of claim 9, wherein said frame grid includes a cross-bar extending between said front and rear sides of said grid, and wherein said third post couples to said grid at said cross-bar.

16. The apparatus of claim 1 wherein said spaced notch segments hold said laparoscopic instruments with a heavier end of said instruments within said segments of said first holding bar and with a lighter end of said instruments within said segments of said second holding bar.

* * * * *